(12) United States Patent
Brown et al.

(10) Patent No.: US 6,589,533 B1
(45) Date of Patent: *Jul. 8, 2003

(54) GENETICALLY-ENGINEERED ALPHAVIRUSES, FLAVIVIRUSES, AND BUNYAVIRUSES WITH MODIFIED ENVELOPE TRANSMEMBRANE GLYCOPROTEINS AND ALTERED HOST-RANGE PHENOTYPE

(75) Inventors: Dennis T. Brown, Raleigh, NC (US); Racquel Hernandez, Raleigh, NC (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/447,103

(22) Filed: Nov. 22, 1999

Related U.S. Application Data

(63) Continuation-in-part of application No. 09/157,270, filed on Sep. 18, 1998, now Pat. No. 6,306,401.
(60) Provisional application No. 60/059,668, filed on Sep. 18, 1997, now abandoned.

(51) Int. Cl.[7] .................................................. A61K 39/12
(52) U.S. Cl. ................................ 424/205.1; 424/218.1; 424/224.1; 435/236; 435/320.1
(58) Field of Search ........................................ 435/320.1

(56) References Cited

U.S. PATENT DOCUMENTS 6,306,401 B1 * 10/2001 Brown et al. ............ 424/218.1

OTHER PUBLICATIONS

Schlesinger, S., and M. J. Schlesinger, 1996, "Togavirdae: the viruses and their replication", in *Fields Virology, Third Edition*, Fields, B. N., et al., eds., Lipincott–Raven Publishers, Philadelphia, pp. 827–829 and 831–834.*
Rice, C. M., 1996, "Flaviviridae: the viruses and their replication", in *Fields Virology, Third Edition*, Fields, B. N., et al., eds., Lipincott–Raven Publishers, Philadelphia, pp. 934, 935, 937, and 938.*
Monath, T. P., and F. X. Heinz, 1996, "Flaviviruses", in *Fields Virology, Third Edition*, Fields, B. N., et al., eds., Lipincott–Raven Publishers, Philadelphia, pp. 961 and 970–974.*
Gonzalez–Scarano, F., and N. Nathanson, 1996, "Buynaviridae", in *Fields Virology, Third Edition*, Fields, B. N., et al., eds., Lipincott–Raven Publishers, Philadelphia, pp. 1473, 1476, 1477, and 1484.*
Liu, L. N., et al., 1996, "Mutations in the endo domain of Sindbis virus glycoprotein E2 block phosphorylation, reorientation of the endo domain, and nucleocapsid binding", Virol. 222:236–246.*
Li, M.–L., et al., 1999, "An amino acid change in the exodomain fo the E2 protein of Sindbis virus, which impairs the release of virus from chicken cells but not from mosquito cells", Virol. 264: 187–194.*
Markoff, L., et al., 1994, "Processing of flavivirus structural glycoproteins: stable membrane insertion of premembrane requires the envelope signal peptide", Virol. 204:526–540.*
Doms, R. W., et al., 1993, "Folding and assembly of viral membrane proteins", Virol. 193:545–562.*

* cited by examiner

*Primary Examiner*—Laurie Scheiner
*Assistant Examiner*—Jeffrey S. Parkin
(74) *Attorney, Agent, or Firm*—Benjamin Aaron Adler

(57) ABSTRACT

The present invention is directed toward genetically-engineered, membrane-enveloped Alphaviruses, Flaviviruses, and Bunyaviruses containing modified viral transmembrane envelope glycoproteins (e.g., E2, E1, E, and G) and bearing altered host-range phenotypes that enables the viruses to replicate efficiently in insect cells, but not mammalian cells. The strategy for production of these mutations is based on the fact that unlike mammalian cell membranes, the membranes of insect cells contain no cholesterol and are thus thinner than mammalian membranes. Many membrane-coated viruses have membrane glycoproteins on their surface which are responsible for identifying and infecting target cells. These membrane glycoproteins have hydrophobic membrane-spanning domains which anchor the proteins in the membrane bilayer. The membrane-spanning domains of these transmembrane proteins must be long enough to reach from one side of the bilayer to the other in order to hold the proteins in the membrane. The transmembrane envelope glycoproteins have been modified by introducing deletions into the membrane spanning domain, said deletions resulting in a modified envelope glycoprotein that is capable of spanning insect cell membranes, but not mammalian cell membranes, and an altered host-range phenotype that enables the virus to infect and produce progeny virus in insect cells, and to infect, but not produce progeny virus, in mammalian cells.

6 Claims, 5 Drawing Sheets

Fig. 4

GENETICALLY-ENGINEERED ALPHAVIRUSES, FLAVIVIRUSES, AND BUNYAVIRUSES WITH MODIFIED ENVELOPE TRANSMEMBRANE GLYCOPROTEINS AND ALTERED HOST-RANGE PHENOTYPE

CROSS-REFERENCE TO RELATED APPLICATION

This patent application is a continuation-in-part of. U.S. application Ser. No. 09/157,270, filed Sep. 18, 1998, now U.S. Pat. No. 6,306,401 which claims benefit of priority under 35 U.S.C. 119(e) of provisional application Ser. No. 60/059,668, filed Sep. 18, 1997, now abandoned.

BACKGROUND OF THE INVENTION

1. Field of the Invention

The present invention relates generally to virology and disease control. Specifically, the present invention relates to mutated arthropod vectored viruses and their uses as vaccines.

2. Description of the Related Art

Arthropod vectored viruses (Arboviruses) are viral agents which are transmitted in nature by blood sucking insects. Many of these viruses have membrane bilayers with associated integral membrane proteins which make up the protective envelope of the virus particle (Togaviruses) (Schlesinger, S. and M. J. Schlesinger, 1990).

Collectively, the arthropod vectored viruses are second only to malaria as a source of insect-transmitted disease and death in man and animals throughout the world (Berge A. O. 1975). Among these viral agents are Eastern, Western, and Venezuelan Equine Encephalitis Viruses, Dengue Fever, Japanese Encephalititis, San Angelo Fever, West Nile Fever and Yellow Fever. Further, diseases caused by these agents are in resurgence in North America (NIAID *Report of the Task Force on Microbiology and Infectious Diseases* 1992, NIH Publication No. 92-3320) as a result of the introduction of the mosquito vector *Aedes albopictus* (Sprenger, and Wuithiranyagool 1985).

By their very nature, Arboviruses must be able to replicate in the tissues of both the invertebrate insect and the mammalian host (Brown, D. T., and L. Condreay, 1986, Bowers et al. 1995). Differences in the genetic and biochemical environment of these two host cell systems provide a basis for the production of viruses which can replicate in one host but not the other (Host Range Mutants).

Currently, Dengue Fever and Eastern Equine Encephalitis and other insect bourne viruses are in resurgence in the United States. The U.S. Army and other government agencies have been trying to make vaccines against these viruses since the 1960s with little success. Thus, the prior art is deficient in a vaccine against most arthropod vectored viruses and other membrane-coated viruses. The present invention fulfills this long-standing need and desire in the art.

SUMMARY OF THE INVENTION

In one embodiment of the present invention, there is provided a genetically engineered, membrane-enveloped virus, wherein the virus codes for a transmembrane protein which has a deletion of one or more amino acids such that the transmembrane protein is able to span or correctly integrate into the viral membrane when the engineered virus replicates in insect cells, but is unable to span or correctly integrate into the viral membrane when the virus replicates in mammalian cells. Preferably, the virus is an Arthropod vectored virus selected from the group consisting of Togaviruses, Flaviviruses, Bunya viruses and all other enveloped viruses which can replicate naturally in both mammalian and insect cells, as well a s other enveloped viruses which can be made to replicate in mammalian and insect cells by genetic engineering of either the virus or the cell. Representative examples of such engineered viruses are ΔK391 virus and TM16 virus.

In another embodiment of the present invention, there is provided a method of producing a viral vaccine from a genetically engineered, membrane-enveloped virus for vaccination of mammals, comprising the steps of producing deletions in the membrane associated domains of the virus which restrict their ability to grow to insect cells, introducing the engineered virus disclosed herein into insect cells and allowing the virus to replicate in the insect cells to produce a viral vaccine. Representative examples of the engineered viruses are ΔK391 virus and TM16 virus.

In still another embodiment of the present invention, there is provided a method for vaccinating an individual in need of such treatment comprising the step of introducing the viral vaccine of the present invention into the individual to produce viral proteins for immune surveillance and stimulate immune system for antibody production.

In still yet another embodiment of the present invention, there is provided a method of producing a viral vaccine from a genetically engineered, membrane-enveloped virus to a disease spread by a wild mosquito population to mammals, comprising the steps of engineering a deletion of one or more amino acids in a viral transmembrane protein to produce an engineered virus, similar to TM16 or delta K391, wherein the transmembrane protein is able to span the membrane envelope when the virus replicates in mosquito cells, but is unable to span the membrane envelope when the virus replicates in mammalian cells, and wherein the virus remains capable of replicating in wild mosquito cells; introducing the engineered virus into the wild mosquito population; and allowing the engineered virus to replicate in cells of the wild mosquito population to produce a population of mosquitoes which harbor the vaccine strain of the virus and exclude the wild type (pathogenic) virus such that the mosquito bite delivers the vaccine to a mammal bitten. Presence of the mutated virus renders the mosquito incapable of transmitting other membrane containing viruses (Karpf et al 1997)

Other and further aspects, features, and advantages of the present invention will be apparent from the following description of one of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 4 shows the deleted amino acids in the E2 transmembranal domain. The deleted sequence is shown under the appropriate amino acid, ranging from 1 to 16 deletions. Histidine and Proline sequences beginning at nt 9717 are on the lumenal side of the protein but are used to design the mutagenic primers.

DETAILED DESCRIPTION OF THE INVENTION

It will be apparent to one skilled in the art that various substitutions and modifications may be made to the invention disclosed herein without departing from the scope and spirit of the invention.

As used herein, the term "membrane-bound virus" refers to a virus which contains a lipid membrane bilayer as part of its protective exterior coat.

As used herein the term "viral envelope" refers to the lipid membrane component of the membrane containing virus and its associated proteins.

As used herein, the terms "arthropod vectored virus" or "Arbovirus" refer to viral agents which replicate and produce progeny virus in arthropod (insect) or mammalian cells. This includes Togaviruses, Flaviviruses and Bunyaviruses.

As used herein, the term "Togavirus" refers to a general classification of membrane containing viruses which include the Alphaviruses.

As used herein, the term "membrane bilayer" refers to a structure consisting of opposed amphiphatic phospholipids. The bilayer is organized in cross section from polar head groups to non-polar carbon chains to nonpolar carbon chains to polar head groups.

As used herein, the term "glycoprotein transmembrane region" refers to the amino acid sequence of the region of a membrane-integrated protein which spans the membrane bilayer.

As used herein, the term "viral vaccine" refers to a strain of virus or virus mutant which has the antigenic properties of the virus but cannot produce disease.

As used herein the term "immune surveillance" refers to a process by which blood lymphocytes survey the cells and tissues of a mammal to determine the presence of foreign (virus) proteins and stimulates the production of lymphocytes capable of targeting cells producing the foreign protein for destruction. This process also leads to the production of circulating antibodies against the foreign protein.

As used herein, the term "infectious virus particles" refers to viruses which are capable of entering a cell and producing virus protein, whether or not they are capable of producing progeny virus.

As used herein, the term "non-infectious virus particles-"refers to viruses which are not capable of infecting or entering a cell.

As used herein, the term "vertebrate cells" refers to any mammalian cell.

As used herein, the term "invertebrate cells" refers to any insect cell.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment. A vector is said to be "pharmacologically acceptable" if its administration can be tolerated by a recipient animal. Such an agent is said to be administered in a "therapeutically effective amount" if the amount administered is physiologically significant. An agent is physiologically significant if its presence results in a change in the physiology of a recipient mammal. For example, in the treatment of viral infection, a compound which decreases the extent of infection or of physiologic damage due to infection, would be considered therapeutically effective.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl)

terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Figure 1:
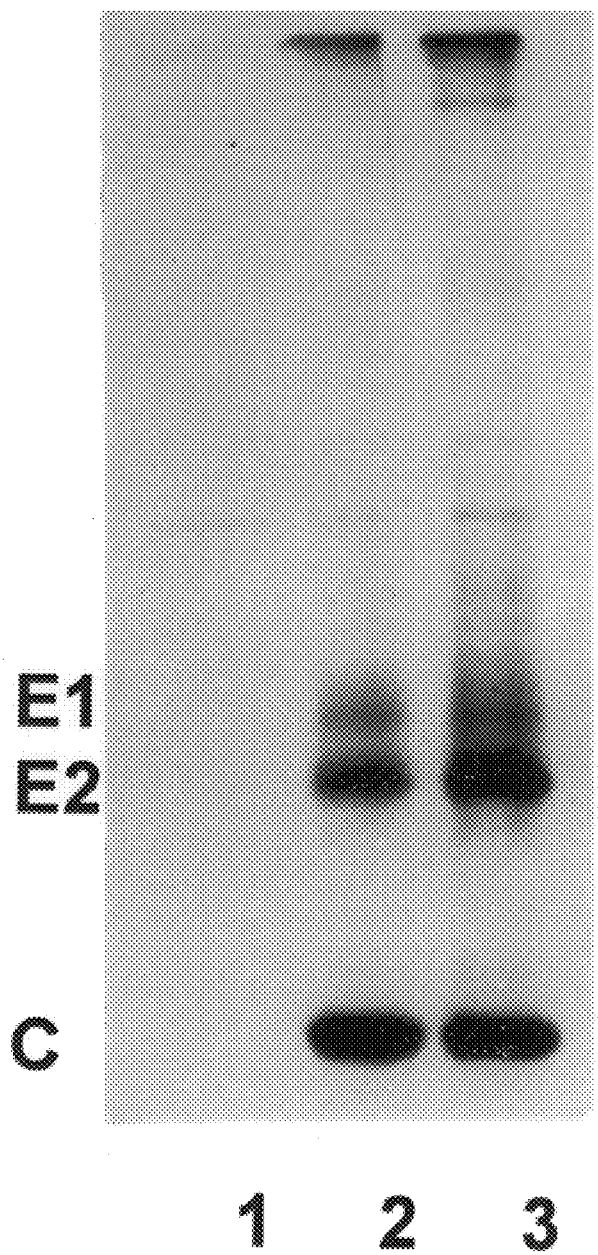
FIG. 1 shows the results of radiolabeled Sindbis virus proteins recovered from transfected tissue-cultured cells. BHK-21 cells mock transfected (1), transfected with mutant Δ391 RNA (2), and *Aedes albopictus* cells transfected with Δ391 RNA (3), were labeled with radioactive amino acids as described in Example 3. At 24 hours post-transfection; proteins were precipitated with virus specific anti-serum as described in Example 4. The figure shows that both BHK-21 cells and *Aedes albopictus* cells transfected with RNA of the deletion mutant produce the three viral structural proteins E1, E2, and C which are not detected in the mock transfected cells.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Various promoters may be used to drive vectors.

The term "oligonucleotide" or "probe" as used herein, refers to a molecule comprised of ribonucleotides or deoxyribonucleotides. The exact size of the oligonucleotide or probe will depend upon many factors which, in turn, depend upon the ultimate function and use of the oligonucleotide. The length of the probe is not critical, but will usually comprise at least about 12 bases, more usually comprising at least about 16 bases, and the probe is substantially complementary to a portion of the bacterial genome; however, the probe need not have perfect complementarity with the genome. The probes may be prepared synthetically, with suitable synthetic techniques, and most likely include a detectable label. Usually, the synthetic sequences are expanded in common, publicly-available cloning vectors and suitable hosts in order to obtain large quantities of the probe. The expanded vectors may themselves be labeled for use as probes, or shorter fragments containing complementary strands may be excised and labeled.

Methods for the preparation and utilization of nucleotide probes for diagnostic testing are described in the references listed above, supra, and in U.S. Pat. No. 4,358,535 to Falkow, et al.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transfected" by exogenous, or heterologous DNA when such DNA has been introduced inside the cell. The transfecting DNA may or may not be integrated (covalently linked) into the genome of the cell. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene).

The present invention is directed to a genetically engineered, membrane-enveloped virus, wherein the virus codes for a transmembrane protein which has a deletion of one or more amino acids in the transmembrane region of the protein such that the transmembrane protein is able to span or correctly integrate into the membrane of an infected cell when the engineered virus replicates in insect cells, but is unable to span or integrate into the membrane of an infected cell when the virus replicates in mammalian cells. Preferably, the virus is an Arthropod vectored virus selected from the group consisting of Togaviruses, Flaviviruses, Bunya viruses and all other enveloped viruses which can replicate naturally in both mammalian and insect cells, as well as enveloped viruses which can be made to replicate in mammalian and insect cells by genetic engineering of either the virus or the cell. Representative examples of such engineered viruses are ΔK391 virus and TM16 virus. Still preferably, the insect cells are mosquito cells, such as *Aedes albopictus cells*, and the mammalian cells are human cells.

In a preferred embodiment, the genetically engineered, membrane-enveloped virus is Sindbis virus, and the transmembrane protein is viral glycoprotein E2. However a person having ordinary skill in this art could readilypredict that similar mutations can be successfully installed in the membrane spanning domains of other virus membrane proteins such as E1.

In another preferred embodiment, the genetically engineered, membrane-enveloped virus is selected from the group consisting of HSV, HIV, rabies virus, Hepatitis, and Respiratory Syncycial virus, and the transmembrane protein is selected from the group consisting of glycoprotein E1, glycoprotein E2, and G protein.

In still another preferred embodiment, the genetically engineered, membrane-enveloped virus are RNA tumor viruses, and the transmembrane protein is Env.

The present invention is also drawn to a method of producing a viral vaccine from the genetically engineered, membrane-enveloped virus disclosed herein for vaccination of mammals, comprising the steps of introducing the engineered virus into insect cells and allowing the virus to replicate in the insect cells to produce a viral vaccine. Representative examples of the engineered viruses are ΔK391 virus and TM16 virus.

In addition, the present invention provides a method for vaccination of an individual in need of such treatment, comprising the steps of introducing the viral vaccine of the present invention into the individual and allowing the vaccine to produce viral proteins for immune surveillance and stimulate immune system for antibody production in the individual.

Further, the present invention provides a method of producing a viral vaccine to a disease spread by a wild mosquito population to a mammal, comprising the steps of genetically engineering a deletion of one or more amino acids in a viral transmembrane protein to produce an engineered virus, wherein the transmembrane protein is able to span the membrane envelope when the virus replicates in mosquito cells, but is unable to span the membrane envelope when the virus replicates in mammalian cells, and wherein the virus remains capable of replicating in mosquito cells; introducing the engineered virus into a wild mosquito population; and allowing the virus to replicate in cells of the wild mosquito population to produce, a population of mosquitos which harbor the vaccine strain of the virus and exclude the wild type (pathogenic) virus such that the mosquito bite delivers the vaccine to a mammal bitten.

It is contemplated that pharmaceutical compositions may be prepared using the novel mutated viruses of the present invention. In such a case, the pharmaceutical composition comprises the novel virus of the present invention and a pharmaceutically acceptable carrier. A person having ordinary skill in this art readily would be able to determine, without undue experimentation, the appropriate dosages and routes of administration of this viral vaccination compound. When used in vivo for therapy, the vaccine of the present invention is administered to the patient or an animal in therapeutically effective amounts, i.e., amounts that immunize the individual being treated from the disease associated with the particular virus. It will normally be administered parenterally, preferably intravenously or subcutaineusly, but other routes of administration will be used as appropriate. The amount of vaccine administered will typically be in the range of about $10^3$ to about $10^6$ pfu/kg of patient weight. The schedule will be continued to optimize effectiveness while balancing negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference. For parenteral administration, the vaccine will be most typically formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin.

The vaccines of the present invention are based on deletion mutations in the transmembrane domains of proteins of membrane-enveloped viruses. The strategy for production of these mutations is based on the following information: Unlike mammalian cell membranes, the membranes of insect cells contain no cholesterol (Clayton 1964, Mitsuhashi et al 1983). The presence of cholesterol in membranes in general makes the membrane thicker, with the increase in thickness increasing as the amount of cholesterol increases (Bretscher, 1993). Many membrane-coated viruses have membrane glycoproteins on their surface which are responsible for identifying and infecting target cells (Schlesinger, S. and M. J. Schlesinger, 1990). These membrane glycoproteins have hydrophobic membrane-spanning domains which anchor the proteins in the membrane bilayer (Rice et al 1982).

The membrane-spanning domains of these transmembrane proteins must be long enough to reach from one side of the bilayer to the other in order to hold or anchor the proteins in the membrane. Experiments have shown that if the domains are shortened by the deletion of amino acids within the domain, the proteins do not appropriately associate with the membrane and fall out (Adams and Rose. 1985).

Because insects have no cholesterol in their membranes, the insect-generated viral membrane will be thinner in cross section than the viral membranes generated from mammals. Since the membranes of insects are thinner, the membrane-spanning domains of proteins integrated into insect membranes do not need to be as long as those integrated into the membranes of mammals. It is possible, therefore, to produce deletions in engineered viruses which remove amino acids from the transmembrane domain of the viral glycoprotein. This results in a glycoprotein which can integrate normally into the membrane of a virus replication in an insect cell, but not into the membrane of a virus replicating in a mammal. Thus, the mutated virus is produced in the insect cell replicating as well as the parent, wildtype virus in the insect host. On the other hand, in mammals, the mutant virus can infect the host producing viral proteins; however because the mutated virus glycoprotein cannot span and be anchored in the mammalian membrane, progeny virus cannot be produced in mammalian cells. An example of such a virus is TM16. An additional advantage to the approach of the present invention is that the mutants are engineered as deletion mutants, hence there is absolutely no chance for reversion to wildtype phenotype, a common problem with virus vaccines.

The vaccines envisioned by the present invention work for any membrane-enveloped viruses which grow in vertebrate and invertebrate cells. Indeed, the present invention is applicable to membrane-enveloped viruses which can be either engineered to grow in an insect cell, or to membrane-enveloped viruses which grow in genetically-modified insect cells.

The following examples are given for the purpose of illustrating various embodiments of the invention and are not meant to limit the present invention in any fashion:

EXAMPLE 1

Site-Directed Mutagenesis of Toto 1101

Using the full length clone of the Alpha virus Sindbis described previously (Liu et al 1996, Rice et al., 1987), a deletion removing 3 bases encoding a lysine at position 391 in the amino acid sequence of the virus glycoprotein E2 has been constructed. This lysine is part of the putative membrane-spanning domain of this protein (Rice et al 1982).

Site-directed mutagenesis was used to generate a deletion mutant (Lys391) in Toto 1101, a plasmid containing the full-length Sindbis cDNA and an SP6 promoter that can be used to transcribe infectious RNA from the clone in vitro (Rice et al., 1987 Liu and Brown, 1993a). Using the megaprimer method of PCR mutagenisis (Sarkar and Sommer, 1990) described previously (Liu and Brown, 1993a), three nucleotides were removed in the cDNA clone of Toto 1101, nucleotides (nts) 9801, 9802, 9803, resulting in the removal of the codon AAA (K391).

A 30 base oligonucleotide of the sequence, 5'CTCACG-GCGCGCACAGGCACATAACACTGC3' (SEQ ID No.: 1) was used as the mutagenesis primer. This primer, along with the "forward primer" 5'CCATCAAGCAGTGCGTCG3' (SEQ ID No.: 2; 18mer), generated a 518 base "Megaprimer" (nucleotides 9295–9813). The second PCR reaction consisted of 0.5 μg of megaprimer, 100 μg Toto 1101 template and 0.5 μg of the "reverse primer" 5' GGCAGTGTGCACCTTAATCGCCTGC 3' (SEQ ID No.: 3). All PCR reactions employed 30 cycles at 95 degrees for 1 min., 64 degrees for 1 min., 72 degrees for 1 min. and a final incubation at 72 degrees for 8 min. The resulting PCR product (1149 nts) was cleaved with BCL I and SPL and inserted into the corresponding site in Toto 1101, creating the deletion mutant K391. After the deletion was confirmed by dideoxynucleotide sequencing through the entire subcloned region using Sequenase™ (U.S. Biochemical, Cleveland, Ohio), infectious RNA was transcribed in vitro using SP6 polymerase and was introduced into BHK-21 cells.

EXAMPLE 2
In vitro Transcription and RNA Transfection

Plasmid DNA containing the full-length cDNA copy of Sindbis virus K391 or wild type RNA was linearized with XhoI and transcribed in vitro with SP6 RNA polymerase as described previously (Rice et. al., 1987). 1 μg of Xho I linearized K391 cDNA or wild type Sindbis virus cDNA was transcribed in buffer consisting of 80 mM Hepes pH 7.5, 12 mM MgCl, 10 mM DTT and 2 mM spermidine and 100 μgm BSA with 3 mM each ATP, UTP, CTP, 1.5 mM GTP and 4.5 mM $m^7$ GpppG, 20 units SP6 RNA polymerase and 20 units RNase inhibitor in a 20 μl reaction volume. After incubation at 37° C. for 2 hours, RNA production was assayed by running 2 μl of the RNA product on a 1% agarose gel.

Baby Hamster Kidney (BHK21) cells and *Aedes albopictus* (mosquito) cells were transfected with RNA derived from the mutant or wild type clone. Mosquito cell transfections were carried out using 5×10⁶ cells resuspended in RNase free electroporation buffer consisting of 20 mM Hepes pH 7.05, 137 mM NaCl, 0.7 mM $Na_2HPO_4$ and 6 mM dextran. Washed cells were resuspended in diethyl pyrocarbonate (depc) treated water (HBS) to a concentration of 5×10⁷ cells/ml. RNA transcripts in 20 μl were added to 400 μl washed cells and transferred to a 0.2 cm gap length cuvette. Optimal electroporation parameters for these cells was found to be 2 KV 25 μF, 8 resistence. Transfected cells were incubated at 37° C. until cytopathic effect was observed (about 24 hours).

After 24 hours of incubation, the media was collected from both infected cell lines as well as non-RNA transfected controls. The media from each cell line was tested for the presence of infectious virus by plaque assay (as described by Renz and Brown 1976) on mosquito and BHK-21 cell monolayers (Table 1).

TABLE 1

Infectious virus produced by transfection of BHK21 or *Aedes albopictus* (AA) cells with Sindbis virus wild type (wt) or mutant K391

| Cell line transfected | BHK Mock[a] Transfected | BHK with wt RNA | BHK with K391 RNA | AA Mock Transfected | AA with wt RNA | AA with K391 RNA |
|---|---|---|---|---|---|---|
| Media titered on BHK | no virus detected | $1.5 \times 10^9$ virus/ml | $3.0 \times 10^3$ | no virus detected | $5.0 \times 10^8$ virus/ml | $1.0 \times 10^8$ |
| Media titered on AA | no virus detected | $8 \times 10^7$ virus/ml | $8.0 \times 10^4$ | no virus detected | $1.0 \times 10^9$ virus/ml | $2.0 \times 10^9$ virus/ml |

[a]Mock indicates that transfection protocol was carried out without RNA

As shown in Table 1, the mutant K391 produces significant amounts of infectious virus particles only when replicating in the insect cell. BHK cells transfected with K391 produced very low levels of virus, 4 to 5 orders of magnitude lower than the amount produced in insect cells.

EXAMPLE 3

Metabolic Radioactive Labeling of Viral Proteins

Subconfluent monolayers of BHK21 cells in 25 $cm^2$ flasks were transfected with wild type or K391 mutant RNA as described above. Monolayers were starved for 30 min in methionine- and cysteine-free medium (MEM-E) containing 1% FCS, 2 mM glutamine and 5% TPB (starvation medium). At 16 hours post-transfection, cells were pulse-labeled with starvation medium containing 50 μCi/ml [$^{35}S$] Met/Cys protein labeling mix for 20 minutes. Labeling was terminated by washing the monolayers with PBS containing 75 μg/ml cycloheximide. Monolayers were chased for 45 minutes in medium containing 10 times the normal concentration of methionine and cysteine and 75 μg/ml cycloheximide.

EXAMPLE 4

Immunoprecipitation and Polyacrylamide Gel Electrophoresis

Radiolabeled viral proteins were immunoprecipitated with antisera as described (Knipfer and Brown, 1989). [$^{35}S$] Met/Cys labeled cells were washed twice in cold PBS and lysed in lysis buffer: 0.5% NP-40, 0.02 M Tris HCl pH 7.4, 0.05 M NaCl, 0.2 mM PMSF, 0.2 mM TPCK and 0.02 mM TLCK. The nuclei were pelleted by centrifugation and discarded. The supernatant was pre-absorbed with 100 μl of protein A/Sepharose beads (Sigma) suspended in lysis buffer for 1 hr, and the beads were pelleted. The pre-absorbed supernatant was treated with 200 μl of protein A/Sepharose beads coupled to rabbit anti-SVHR serum or E2 tail mono-specific polyclonal serum and agitated overnight at 4° C.

The immunoprecipitated bead-antibody-protein complexes were washed three times with lysis buffer and then solubilized in SDS-PAGE sample buffer consisting of 12% glycerol, 4% SDS, 50 mM Tris pH 6.8, 5% mercaptoethanol and 0.02% bromphenol blue. The samples were heated for 3 min at 95° C. and the beads were removed from the sample by centrifugation. Gel electrophoresis was carried out on a 10.8% SDS PAGE or 16% Tricine gel as described previously (Liu and Brown, 1993 a,b). Fluorography was performed as described (Bonner and Laskey, 1974) and dried gels were exposed to Kodak XAR-5 film (see FIG. 1).

EXAMPLE 5
Transmission Electron Microscopy

BHK-21 cell monolayers infected with K391 produced from transfected mosquito cells or transfected with K391 RNA were lifted from flasks by trypsin treatment at desired time points, and the cells were pelleted by low speed centrifugation. Cell pellets were washed twice in PBS and fixed in 4% glutaraldehyde at 4° C. overnight. The cells were then washed three times with 0.2 M cacodylate buffer (pH 7.2), post-fixed with 2% osmium tetroxide for 1 hour at room temperature, and washed three times in cacodylate buffer. The cells were stained en bloc for 1 hr at room temperature with 0.5% uranyl acetate. After three washes, cell pellets were embedded in 1% agarose and dehydrated through a graded ethanol/acetone series. Final embedding was in Mollenhauer's (1964) Epon-Araldite epoxy mixture #1 at 70° C. for two days. Ultrathin sections were cut on a Sorvall MT5000 microtome and collected on 150 mesh copper grids. Sections were stained with 1% uranyl acetate and/or lead citrate and were photographed in a Jeol 100CX transmission electron microscope. (see FIG. 2).

Figure 2A:
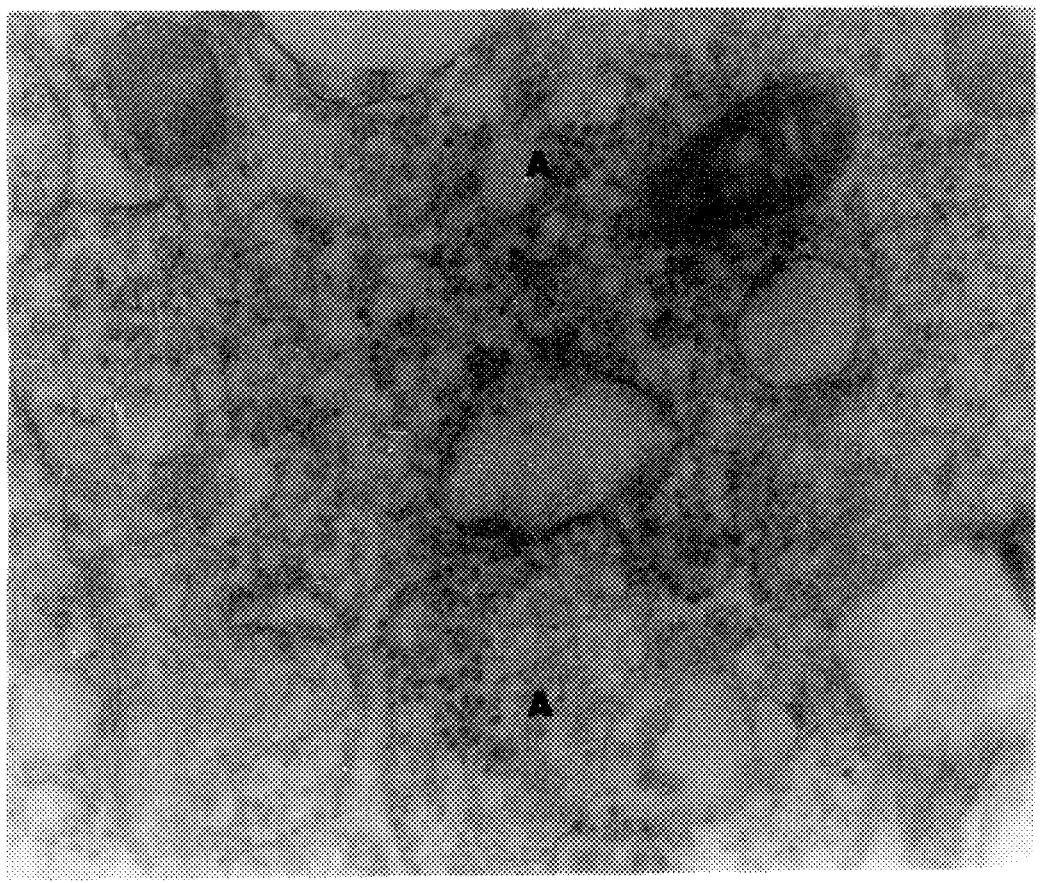
FIGS. 2A and 2B are electron micrographs of BHK-21 cells (2A) and *Aedes albopictus* cells (2B) transfected with RNA of the Sindbis virus deletion mutant Δ391. Cells were transfected as described in Example 2. BHK-21 cells (FIG. 2A) show clusters of virus core structures in the cell cytoplasm (A) even though these cells produce very low levels of mature virus (Table. 1). *Aedes albopictus* cells (FIG. 2B) also produce clusters of virus cores; however, these cores are found free in the cells' cytoplasm similar to those in BHK-21 cells (A) and are: also found associated with cell membranes (B). This latter case is not found in BHK-21 cells, indicating that the glycoproteins E1 and E2, although present, do not function to bind them.
Figure 2B:
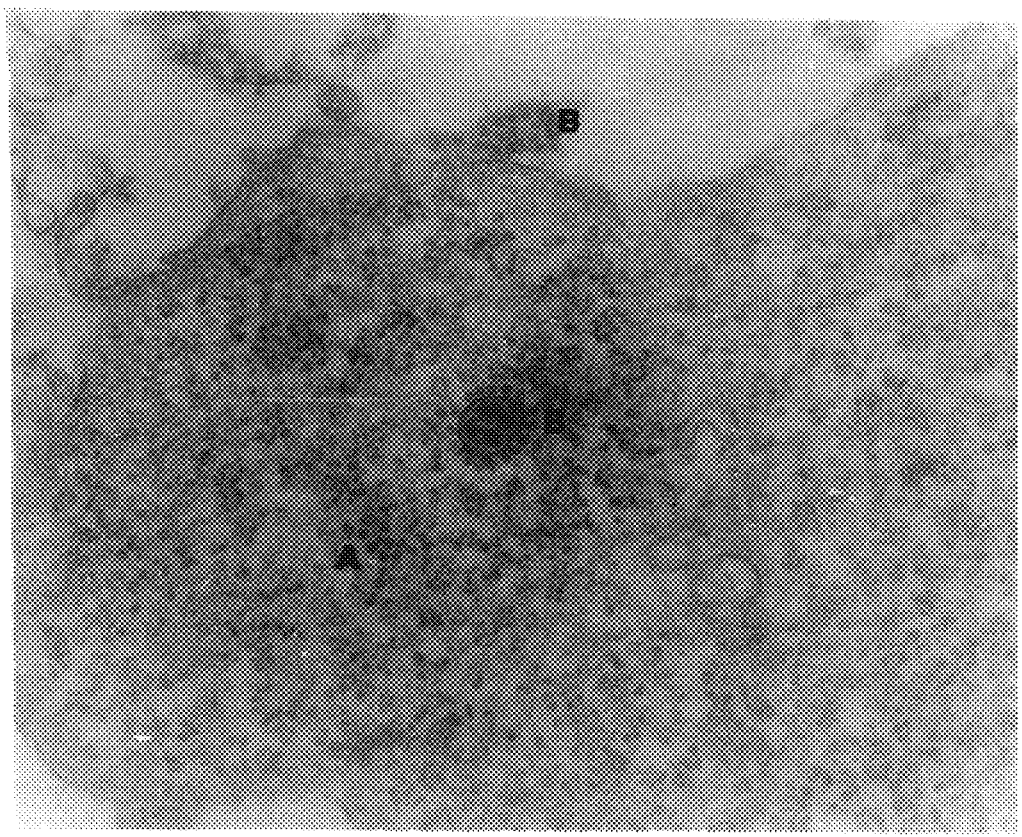

Although BHK cells infected with K391 virus or transfected with K391 RNA produce no virus detectable by the plaque assay, it was shown by PAGE that they do produce all virus structural proteins (FIG. 1). Further, it was shown by electron microscopy that they assemble the intracellular (non infectious) virus cores (FIG. 2).

EXAMPLE 6
Uses for the Sindbis Deletion Mutant K391 and Similar Mutations Produced in Other Togaviruses Delta K391 produces very high titers of mutant Sindbis virus particles when allowed to replicate in mosquito cells. The exposed regions of the proteins (ecto domains) are wild type in sequence. These wild type proteins allow the virus to enter mammalian cells and produce virus proteins (see FIG. 1) but new virus is not assembled as shown by electron microscopy in FIG. 2.

Delta K391 is a vaccine strain. It is produced in very high concentration in cultured insect cells. However, when the virus is injected into a mammalian host, the virus circulates and infects cells in a mammalian host, these infected cells produce and present virus proteins for immune surveillance, but, because of the truncation in the membrane domain, the infection will be limited primarily to those cells infected initially by the innoculum. Because the vaccine strain is the result of a deletion mutation, reversion to wild type pathogenic phenotype is not possible.

Further, an engineered deletion mutant may be introduced into the wild mosquito population. It has been shown that these viruses are spread from the female parent to the progeny by a process of transovariol transmission (Leakey 1984). When these mosquitoes bite a vertebrate they will provide an immunizing dose ($10^6$ infectious particles) of the vaccine strain (for example, Delta K391). Karpf et al (1997) showed that infection of insect cells by one Alpha virus prevents the cells from being infected by another, even distantly-related alpha virus for an indefinite amount of time (over two years in cell culture, where the life of a mosquito is 28 days). Thus, the presence of the vaccine strain (for example Sindbis Delta K391 or TM16) will block the spread of other related and pathogenic viruses by these insects.

EXAMPLE 7
Additional Deletion Mutations

Additional deletion mutations in the membrane spanning domain of Sindbis virus glycoprotein E2 were prepared. The protocol for production of these deletion mutations is described below. The procedure is described for the model membrane containing virus Sindbis, however, the procedure can be easily applied to any other virus membrane glycoprotein.

Figure 3:
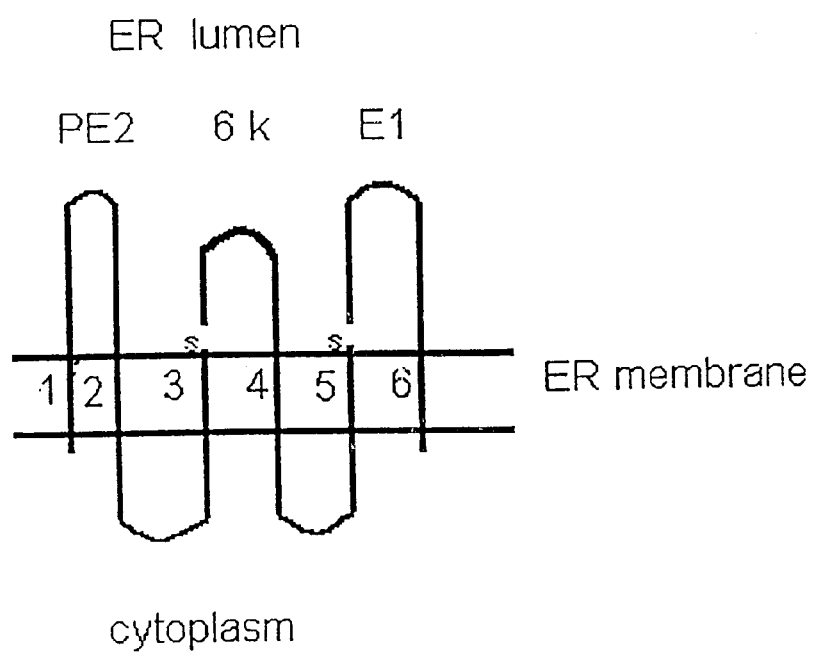
FIG. 3 shows the configuration of Sindbis virus glycoproteins after integration into the ER. The protein is a multipass protein with 6 membrane spanning domains (numbered 1–6). 1. The signal sequence for initial integration; 2. The first E2 transmembrane domain (TMD); 3. The second E2 TMD; 4. The first 6k TMD; 5. The second 6k TMD; and 6. The E1 TMD. S=point of cleavage by signal peptidase.

The envelope glycoproteins of Sindbis virus are integrated into the membranes of the endoplasmic reticulum as a multi pass protein with 6 membrane spanning domains. There are, therefore, 6 potential targets for the production of deletion mutations which will prevent the correct integration of a transmembrane domain (TMD) (See FIG. 3). Some of these targets are less satisfactory for this procedure than others. TMD #1 (FIG. 3 ) is the signal sequence which is recognized by the Signal Recognition Particle and directs protein synthesis to the membranes of the ER Truncating this domain would likely disturb targeting in both mammalian and insect cells. TMD #3 contains the protein sequence of E2 which recognizes and binds capsid protein. It has been shown that this interaction is very specific in nature and requires the sequence that is in the transmembrane domain (Liu et al., 1996; Lopez et al., 1994). TMD#3, therefore, like TMD #1 has a functional as well as a structural component. A significant deletion in this domain would likely eliminate budding in both cell systems. This leaves four transmembrane domains which are targets for the production of deletions which will effect membrane integration (FIG. 3., TMD #2, #4, #5, and #6).

The 6k protein is not a component of mature virus and its function in virus assembly is not clear. In the poly protein the proper integration and orientation of 6k in the ER membrane is essential for the correct integration of E1. The transmembrane domains of 6k (TMD #4 and #5) are excellent targets for deletion mutation as failure to integrate one of these domains may cause the poly protein to integrate into the membrane in a wrong configuration or cause the failure to integrate E1. TMD #2 and #6 are the membrane spanning domains of E2 and E1 and are both obvious targets for deletion mutation. Multiple membrane spanning domains in this poly protein suggest that if deletion mutations in a single transmembrane domain do not totally block virus production in mammalian cells, then deletions in additional membrane spanning domains can further reduce maturation to negligible levels.

EXAMPLE 8
Design of Mutagenic Primers for the E2 Hydrophobic Membrane Anchor (TMD#2)

Protocols for testing the requirements placed on the transmembrane domain of E2 (FIG. 3, TMD #2) is given. This protocol can be easily replicated for any other of the Sindbis membrane spanning domains or the membrane spanning domains of any other virus glycoprotein. The hydrophobic Sindbis PE2 membrane anchor consists of 26 amino acids. As is common with other membrane spanning domains little amino acid homology is conserved among the alphaviruses, although the length of this hydrophobic region is highly conserved (Strauss and Strauss, 1994). The lack of sequence conservation in this domain suggests that it is the hydrophobic properties of the domain and not its sequence which is critical for integration.

Figure 4:
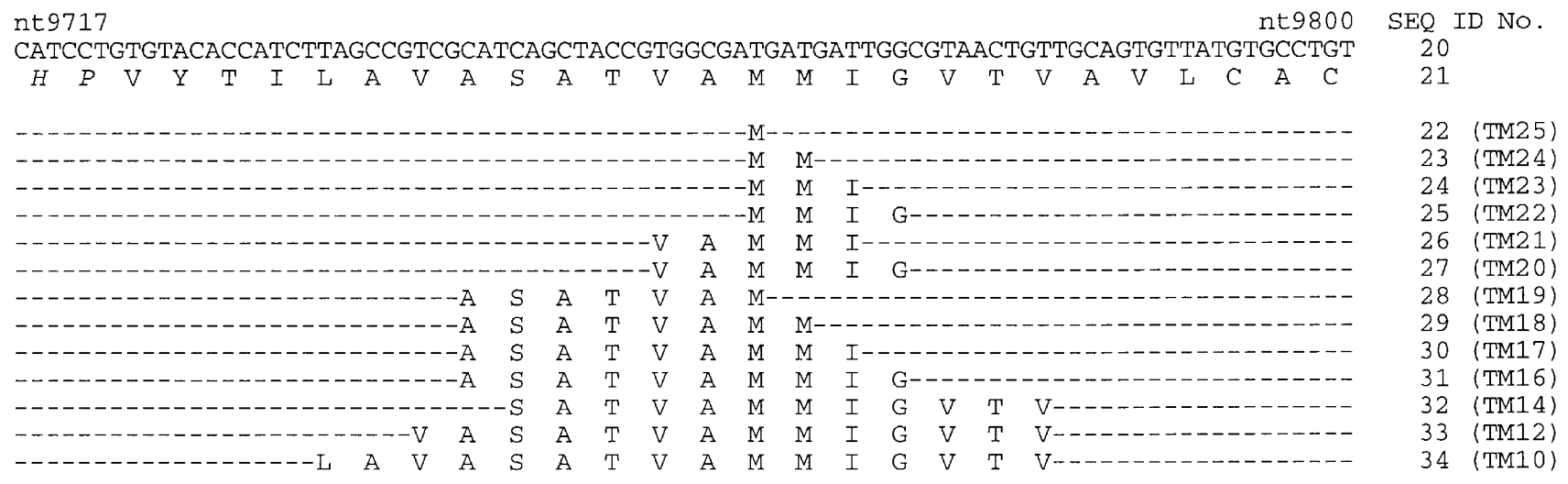

The transmembrane domain of E2 begins at amino acid 365 of the PE2 sequence. This hydrophobic region consists of the sequence: VYTILAVASATVAMMIGVTVAVLCAC (SEQ ID No.: 4). Adams and Rose (1985) demonstrated that a minimum of 14 amino acids in the transmembrane domain of the VSV G protein were necessary for proper anchoring in mammalian cells. Therefore, mutagenic primers have been designed which create a nested set of deletions in the E2 transmembrane domain. Beginning with a deletion of 16 amino acids (which leaves 10 amino acids in the hydrophobic region), a set of deletions were constructed which delete from as many as 16 amino acids, to as few as 1 amino acid from the membrane anchor (FIG. 4).

Deletions were constructed using PCR megaprimer mutagenesis to generate deleted fragments containing unique BclI and SplI sites. All resulting constructs were installed into the wt Sindbis cDNA construct Toto Y420 to generate the mutant plasmids. After linearization with XhoI and transcription using SP6 polymerase, transcripts were transfected into BHK or Aedes albopictus cells by electroporation (as described above). Production of infectious virus from these transfections were titered on both BHK and C710 mosquito cells to determine the host range of these constructs. Table 2 shows the deleted sequences and the primer sequences used in their construction.

For each construct the same primer pair is used to generate the entire BclI to SplI region. The forward primer E1Bcl21 is comprised of the sequence from nucleotide 9306–9327 and reads from $5^1$-$3^{1'}$ GCGTCGCCTATAA-GAGCGACC (SEQ ID No.: 5). The reverse primer Splext is comprised of the sequence from nucleotide 10420–10444 which is the complementary sequence reading from $5^1$-$3^1$ CAGTGTGCACCTTAATCGCCTGC (SEQ ID No.:6).

The virus produced by transfection of insect cells is tested for its ability to produce plaques in BHK and C7–10 mosquito cells as for the mutant E2 ΔK391. Those mutants which do not produce plaques in BHK cells are tested for their ability to infect BHK cell relative to wild type virus by immunofluorescence assay of infected monolayers. This later assay is compared to the total protein in purified preparations of the mutant and wild type virus to establish the relative infectivity of each mutant population. The goal is to truncate the transmembrane domain as much as possible and still obtain reasonable amounts of virus in C7–10 mosquito cell monolayers which can infect but not produce mature virus in BHK cells. If the circumstance arises that truncation of a single transmembrane domain reduces but does not eliminate virus growth in BHK cells a second domain will be truncated and so fourth up to four domains.

TABLE 2

Listing of the deletions in Sindbis E2 and the primers used

| Primer-Designated by No. of Transmembranal Amino Acids | Nucleotides Deleted | Oligonucleotide Sequence of Mutagenic Primer (Negative Strand) |
| --- | --- | --- |
| E2 TM10 | 9734–9782 | ACATAACACTGCGATGGTGTACAC (SEQ ID No.: 7) |
| E2 TM12 | 9740–9782 | ACATAACACTGCGGCTAAGATGG (SEQ ID No.: 8) |
| E2 TM14 | 9746–9782 | ACATAACACTGCTGCGACGGCT (SEQ ID No.: 9) |
| E2 TM16 | 9743–9773 | GCAACAGTTACGACGGCTAAG (SEQ ID No.: 10) |
| E2 TM17 | 9743–9770 | ACAGTTACGCCGACGGCTAAG (SEQ ID No.: 11) |
| E2 TM18 | 9743–9767 | GTTACGCCAATGACGGCTAAG (SEQ ID No.: 12) |
| E2 TM19 | 9743–9764 | CGCCAATCATGACGGCTAAGA (SEQ ID No.: 13) |
| E2 TM20 | 9755–9773 | GCAACAGTTACGGTAGCTGA (SEQ ID No.: 14) |
| E2 TM21 | 9755–9770 | AGTTACGCCGGTAGCTGA (SEQ ID No.: 15) |
| E2 TM22 | 9761–9773 | TGCAACAGTTACCGCCACGGT (SEQ ID No.: 16) |
| E2 TM23 | 9761–9770 | ACAGTTACGCCCGCCACGGT (SEQ ID No.: 17) |
| E2 TM24 | 9761–9767 | GTTACGCCAATCGCCACGGT (SEQ ID No.: 18) |
| E2 TM25 | 9761–9764 | ACGCCAATCATCGCCACGGT (SEQ ID No.: 19) |

This protocol described by the present invention works or any virus which replicates in insects and mammals and has integral membrane proteins as part of its structure, namely, Togaviruses, Flaviviruses and Bunya viruses and all other enveloped viruses which can replicate naturally in both mammalian and insect cells, as well as enveloped viruses which can be made to replicate in mammalian and insect cells by genetic engineering of either the virus or the cell.

Vaccines are made against any membrane-containing virus by removing amino acids from the membrane-spanning domain of a protein in the viral envelope. This is done by removing bases from a cDNA clone of the virus as described. RNA transcribed from the altered clone is transfected into insect cells. The virus produced is amplified by repeated growth in insect cells until large quantities of mutant virus are obtained. This virus is tested for its ability to infect and produce progeny in mammalian cells. Virus which does not produce progeny in mammalian cells are tested for ability to produce immunity in laboratory animals. Those which do produce immunity are candidates for production of human and animal vaccines as is known in the art. This protocol is employed with any arbovirus or other enveloped viruses.

EXAMPLE 9
The Growth of Deletion Mutants

Table 3 shows the growth of the deletion mutants TM12, TM16 and ΔK391 compared to the wild type strain.

TABLE 3

Replication of Sindbis Trans-Membrane Domain Mutants

| Growth in Cell Line | Wild Type | TM12 | TM16 | ΔK391 |
|---|---|---|---|---|
| BHK21 | $3.5 \times 10^8$ | $3.0 \times 10^5$ | $3.4 \times 10^4$ | $1.5 \times 10^4$ |
| A. albopictus | $1.8 \times 10^8$ | $4.5 \times 10^4$ | $1.5 \times 10^8$ | $6.0 \times 10^9$ |

Other deletion mutants, other than TM12 and TM,16, have been made including utants TM10, TM 14 and TM 17. Infection data is collected. TM 10 may not be as useful as TM12 is already too short to replicate in either cell type. TM 14 may be interesting but it may not work better than TM 16. It will likely not work as well. TM 17 like TM 14 may or may not produce the differential titre seen.

As described in Example 8, TM12 deletes 14 amino acids (nucleotides 9740–9782 deleted, Table 2) from the membrane spanning domain of the glycoprotein. TM16 deletes 10 amino acids (nucleotides 9743–9773 deleted, Table 2) from the membrane spanning domain. The data (Table 3) demonstrate that TM12 grows poorly in both the insect and mammalian cells, while TM16 grows to very high levels in insect cells but poorly (4 orders of magnitude lower) in mammalian cells. In this regard, TM16 is like ΔK391. However, since TM16 has a larger size deletion (10 amino acids deleted) compared to single deletion mutant ΔK391, TM16 should be a better vaccine candidate than ΔK391 as the large size deletion insures that the mutant virus cannot revert to wild type phenotype.

The following references were cited herein:

Adams G. A. and Rose J. K. (1985) Structural requirements of a membrane-spanning domain for protein anchoring and cell surface transport. Cell. 41(3):1007–15

Berge, T. O. (ed.) (1975): *International Catalogue of Arboviruses;* 2nd ed., DHEW Publ. No. (CDC) 75–8301 (U.S. Government Office, Washington, D.C.)

Bonner, W. M., and R. A. Laskey. 1974. A film detection method for tritium-labeled proteins and nucleic acids in polyacrylamide gels. Eur. J. Biochem. 46:83–88.

Bowers, D. F., B. A. Abell and D. T. Brown (1995). Replication and Tissue Tropism of the Alphavirus Sindbis in the Mosquito *Aedes Albopictus.* Virology 212: 1–12

Bretscher M S. (1993)Cholesterol and the Golgi apparatus. Science. 261(5126):1280–1

Brown, D. T., and L. Condreay (1986). Replication of alphaviruses in mosquito cells. In The Togaviridae and Flaviviridae. S. Schlesinger (ed.), pp. 473–501.

Clayton, R. B. 1964 The utilization of sterols by insects. J. lipid res. 5:3–19

Karpf, A. R., E. Lenches, J. H. Strauss and D. T. Brown (1997) Superinfection Exclusion of Alphaviruses in Three Mosquito Cell lines Persistently Infected with Sindbis Virus. J. Virol.71:7119–7123.

Knipfer, M. E., and D. T. Brown. 1989. Intracellular transport and processing of Sindbis virus glycoproteins. Virology 170:117–122.

Leake, C. J. (1984). Transovarial transmission of arboviruses by mosquitoes. In Vectors in Virus Biology (Mayo and Harrap, eds.), pp. 63–92. Academic Press.

Liu, N., and D. T. Brown (1993a). Transient translocation of the cytoplasmic (endo) domain of a type-I membrane glycoprotein into cellular membranes. J. Cell Biol. 120:877–883.

Liu, N., and D. T. Brown (1993b). Phosphorylation dephosphorylation events play critical roles in Sindbis virus maturation. J. Virol., 196:703–711.

Liu N., H. Lee, R. Hernandez and D. T. Brown(1996) Mutations in the Endo Domain of Sindbis Glycoprotein E2 Block Phosphorylation, Reorientation of the Endo Domain and Nucleocapsid Binding. Virology 222: 236–246.

Mitsuhashi et al 1983. Sterol free eucaryotic cells from continuous cell lines of insects. Cell Biol. Int. Rep. 7:1057–1062.

Mollenhauer, H. H. 1964. Plastic embedding mixture for use in electron microscopy. Stain Techn. 39:111–114.

NIAID Report of the Task Force on Microbiology and Infectious Diseases (1992). NIH Publication No. 92-3320.

Renz, D., and D. T. Brown. 1976. Characteristics of Sindbis virus temperature-sensitive mutants in cultured BHK-21 and *Aedes albopictus* (mosquito) cells. J. Virol. 19:775–781.

Rice C. M. et al 1982. Isolation and characterization of the hydrophobic COOH-terminal domains of Sindbis virus glycoproteins. J.Mol.Biol. 154:355–378

Rice., C. M., R. Levis, J. H. Strauss, and H. V. Huang. 1987. Production of infectious RNA transcripts from Sindbis virus cDNA clones: mapping of lethal mutations, rescue of a temperature-sensitive marker, and in vitro mutagenesis to generate defined mutants. J. Virol. 61:3809–3819.

Sarkar, G., and S. S. Sommer. 1990. The "megaprimer" method of site-directed mutagenesis. BioTechniques. 8:404–407.

Schlesinger, S. and M. J. Schlesinger (1990). "Replication of Togaviridae and Flaviviridae." (D. M. Knipe and B. N. Fields, eds.), In Virology Vol. I, pp. 697–711. Raven Press, Ltd., New York.

Sprenger, D. and T. Wuithiranyagool (1985). The discovery and distribution of *Aedes albopictus* in Harris County, Tex. J. Am. Mosquito Control Assoc. 2:217–219

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of t he claims.

SEQUENCE LISTING

<160> NUMBER OF SEQ ID NOS: 34

<210> SEQ ID NO 1
<211> LENGTH: 30
<212> TYPE: DNA
<213> ORGANISM: artificial sequence
<220> FEATURE:
<223> OTHER INFORMATION: Used as the mutagenesis primer with the
      "forward primer" to generate a 518 base "Megaprimer" corresponding
      to nucleotides 9295-9813.

<400> SEQUENCE: 1
ctcacggcgc gcacaggcac ataacactgc                                              30

<210> SEQ ID NO 2
<211> LENGTH: 18
<212> TYPE: DNA
<213> ORGANISM: artificial sequence
<220> FEATURE:
<223> OTHER INFORMATION: Used as the "forward primer" with the
      mutagenesis primer to generate a 518 base megaprimer corresponding
      to nucleotides 9295-9813.

<400> SEQUENCE: 2
ccatcaagca gtgcgtcg                                                           18

<210> SEQ ID NO 3
<211> LENGTH: 25
<212> TYPE: DNA
<213> ORGANISM: artificial sequence
<220> FEATURE:
<223> OTHER INFORMATION: Used as the "reverse primer" with the
      megaprimer and the Toto 1101 plasmid template to create 1149
      nucleotide product used to create the deletion mutant K391 in Toto
      1101.

<400> SEQUENCE: 3
ggcagtgtgc accttaatcg cctgc                                                   25

<210> SEQ ID NO 4
<211> LENGTH: 26
<212> TYPE: PRT
<213> ORGANISM: Sindbis virus
<220> FEATURE:
<221> NAME/KEY: transmembrane domain of E2 in the PE2 sequence
<222> LOCATION: 365..390

<400> SEQUENCE: 4

Val Tyr Thr Ile Leu Ala Val Ala Ser Ala Thr Val Ala Met Met
            5                   10                  15

Ile Gly Val Thr Val Ala Val Leu Cys Ala Cys
            20                  25

<210> SEQ ID NO 5
<211> LENGTH: 21
<212> TYPE: DNA
<213> ORGANISM: artificial sequence
<220> FEATURE:
<222> LOCATION: 9306-9327
<223> OTHER INFORMATION: Forward primer E1Bcl21 from megaprimer used
      with reverse primer to generate deletion constructs containing
      unique BclI and SplI sites.

<400> SEQUENCE: 5
gcgtcgccta taagagcgac c                                                       21

<210> SEQ ID NO 6
<211> LENGTH: 23
<212> TYPE: DNA
<213> ORGANISM: artificial sequence
<220> FEATURE:
<222> LOCATION: 10420-10444
<223> OTHER INFORMATION: Reverse primer SpIext from megaprimer used with
      forward primer to generate deletion constructs containing unique
      BclI and SplI sites.

<400> SEQUENCE: 6
cagtgtgcac cttaatcgcc tgc                                           23

<210> SEQ ID NO 7
<211> LENGTH: 24
<212> TYPE: DNA
<213> ORGANISM: artificial sequence
<220> FEATURE:
<223> OTHER INFORMATION: Mutagenic primer E2 TM10 (negative strand) used
      to create a deletion in the E2 transmembranal domain in the
      Sindbis viral glycoprotein.

<400> SEQUENCE: 7
acataacact gcgatggtgt acac                                          24

<210> SEQ ID NO 8
<211> LENGTH: 23
<212> TYPE: DNA
<213> ORGANISM: artificial sequence
<220> FEATURE:
<223> OTHER INFORMATION: Mutagenic primer E2 TM12 (negative strand) used
      to create a deletion in the E2 transmembranal domain in the
      Sindbis viral glycoprotein.

<400> SEQUENCE: 8
acataacact gcggctaaga tgg                                           23

<210> SEQ ID NO 9
<211> LENGTH: 22
<212> TYPE: DNA
<213> ORGANISM: artificial sequence
<220> FEATURE:
<223> OTHER INFORMATION: Mutagenic primer E2 TM14 (negative strand) used
      to create a deletion in the E2 transmembranal domain in the
      Sindbis viral glycoprotein.

<400> SEQUENCE: 9
acataacact gctgcgacgg ct                                            22

<210> SEQ ID NO 10
<211> LENGTH: 21
<212> TYPE: DNA
<213> ORGANISM: artificial sequence
<220> FEATURE:
<223> OTHER INFORMATION: Mutagenic primer E2 TM16 (negative strand) used
      to create a deletion in the E2 transmembranal domain in the
      Sindbis viral glycoprotein.

<400> SEQUENCE: 10
gcaacagtta cgacggctaa g                                             21

<210> SEQ ID NO 11
<211> LENGTH: 21
<212> TYPE: DNA
<213> ORGANISM: artificial sequence
<220> FEATURE:
<223> OTHER INFORMATION: Mutagenic primer E2 TM17 (negative strand) used
      to create a deletion in the E2 transmembranal domain in the Sindbis viral glycoprotein.

<400> SEQUENCE: 11
acagttacgc cgacggctaa g                                                    21

<210> SEQ ID NO 12
<211> LENGTH: 21
<212> TYPE: DNA
<213> ORGANISM: artificial sequence
<220> FEATURE:
<223> OTHER INFORMATION: Mutagenic primer E2 TM18 (negative strand) used
      to create a deletion in the E2 transmembranal domain in the
      Sindbis viral glycoprotein.

<400> SEQUENCE: 12
gttacgccaa tgacggctaa g                                                    21

<210> SEQ ID NO 13
<211> LENGTH: 21
<212> TYPE: DNA
<213> ORGANISM: artificial sequence
<220> FEATURE:
<223> OTHER INFORMATION: Mutagenic primer E2 TM19 (negative strand) used
      to create a deletion in the E2 transmembranal domain in the
      Sindbis viral glycoprotein.

<400> SEQUENCE: 13
cgccaatcat gacggctaag a                                                    21

<210> SEQ ID NO 14
<211> LENGTH: 20
<212> TYPE: DNA
<213> ORGANISM: artificial sequence
<220> FEATURE:
<223> OTHER INFORMATION: Mutagenic primer E2 TM20 (negative strand) used
      to create a deletion in the E2 transmembranal domain in the
      Sindbis viral glycoprotein.

<400> SEQUENCE: 14
gcaacagtta cggtagctga                                                      20

<210> SEQ ID NO 15
<211> LENGTH: 18
<212> TYPE: DNA
<213> ORGANISM: artificial sequence
<220> FEATURE:
<223> OTHER INFORMATION: Mutagenic primer E2 TM21 (negative strand) used
      to create a deletion in the E2 transmembranal domain in the
      Sindbis viral glycoprotein.

<400> SEQUENCE: 15
agttacgccg gtagctga                                                        18

<210> SEQ ID NO 16
<211> LENGTH: 21
<212> TYPE: DNA
<213> ORGANISM: artificial sequence
<220> FEATURE:
<223> OTHER INFORMATION: Mutagenic primer E2 TM22 (negative strand) used
      to create a deletion in the E2 transmembranal domain in the
      Sindbis viral glycoprotein.

<400> SEQUENCE: 16
tgcaacagtt accgccacgg t                                                    21

<210> SEQ ID NO 17
<211> LENGTH: 20

```
<212> TYPE: DNA
<213> ORGANISM: artificial sequence
<220> FEATURE:
<223> OTHER INFORMATION: Mutagenic primer E2 TM23 (negative strand) used
      to create a deletion in the E2 transmembranal domain in the
      Sindbis viral glycoprotein.

<400> SEQUENCE: 17
acagttacgc ccgccacggt                                              20

<210> SEQ ID NO 18
<211> LENGTH: 20
<212> TYPE: DNA
<213> ORGANISM: artificial sequence
<220> FEATURE:
<223> OTHER INFORMATION: Mutagenic primer E2 TM24 (negative strand) used
      to create a deletion in the E2 transmembranal domain in the
      Sindbis viral glycoprotein.

<400> SEQUENCE: 18
gttacgccaa tcgccacggt                                              20

<210> SEQ ID NO 19
<211> LENGTH: 20
<212> TYPE: DNA
<213> ORGANISM: artificial sequence
<220> FEATURE:
<223> OTHER INFORMATION: Mutagenic primer E2 TM25 (negative strand) used
      to create a deletion in the E2 transmembranal domain in the
      Sindbis viral glycoprotein.

<400> SEQUENCE: 19
acgccaatca tcgccacggt                                              20

<210> SEQ ID NO 20
<211> LENGTH: 84
<212> TYPE: DNA
<213> ORGANISM: Sindbis virus
<220> FEATURE:
<221> NAME/KEY: nucleotide sequence of the E2 transmembranal
      domain of the Sindbis viral glycoprotein
<222> LOCATION: 9717..9800

<400> SEQUENCE: 20
catcctgtgt acaccatctt agccgtcgca tcagctaccg tggcgatgat              50
gattggcgta actgttgcag tgttatgtgc ctgt                              84

<210> SEQ ID NO 21
<211> LENGTH: 28
<212> TYPE: PRT
<213> ORGANISM: Sindbis virus
<220> FEATURE:
<221> NAME/KEY: amino acid sequence of the E2 transmembranal
      domain of the Sindbis viral glycoprotein
<222> LOCATION: 363..390

<400> SEQUENCE: 21

His Pro Val Tyr Thr Ile Leu Ala Val Ala Ser Ala Thr Val Ala
                 5                  10                  15

Met Met Ile Gly Val Thr Val Ala Val Leu Cys Ala Cys
                20                  25

<210> SEQ ID NO 22
<211> LENGTH: 27
<212> TYPE: PRT
<213> ORGANISM: artificial sequence
<220> FEATURE:
```

<223> OTHER INFORMATION: Sequence of the E2 transmembranal domain of the
     Sindbis viral glycoprotein after deleting amino acid 378, the
     resulting deletion mutant is TM25.

<400> SEQUENCE: 22

His Pro Val Tyr Thr Ile Leu Ala Val Ala Ser Ala Thr Val Ala
              5                  10                  15

Met Ile Gly Val Thr Val Ala Val Leu Cys Ala Cys
             20                  25

<210> SEQ ID NO 23
<211> LENGTH: 26
<212> TYPE: PRT
<213> ORGANISM: artificial sequence
<220> FEATURE:
<223> OTHER INFORMATION: Sequence of the E2 transmembranal domain of the
     Sindbis viral glycoprotein after deleting amino acids 378 and 379,
     the resulting deletion mutant is TM24

<400> SEQUENCE: 23

His Pro Val Tyr Thr Ile Leu Ala Val Ala Ser Ala Thr Val Ala
              5                  10                  15

Ile Gly Val Thr Val Ala Val Leu Cys Ala Cys
             20                  25

<210> SEQ ID NO 24
<211> LENGTH: 25
<212> TYPE: PRT
<213> ORGANISM: artificial sequence
<220> FEATURE:
<223> OTHER INFORMATION: Sequence of the E2 transmembranal domain of the
     Sindbis viral glycoprotein after deleting amino acids 378 through
     380, the resulting deletion mutant is TM23

<400> SEQUENCE: 24

His Pro Val Tyr Thr Ile Leu Ala Val Ala Ser Ala Thr Val Ala
              5                  10                  15

Gly Val Thr Val Ala Val Leu Cys Ala Cys
             20                  25

<210> SEQ ID NO 25
<211> LENGTH: 24
<212> TYPE: PRT
<213> ORGANISM: artificial sequence
<220> FEATURE:
<223> OTHER INFORMATION: Sequence of the E2 transmembranal domain of the
     Sindbis viral glycoprotein after deleting amino acids 378 through
     381, the resulting deletion mutant is TM22.

<400> SEQUENCE: 25

His Pro Val Tyr Thr Ile Leu Ala Val Ala Ser Ala Thr Val Ala
              5                  10                  15

Val Thr Val Ala Val Leu Cys Ala Cys
             20

<210> SEQ ID NO 26
<211> LENGTH: 23
<212> TYPE: PRT
<213> ORGANISM: artificial sequence
<220> FEATURE:
<223> OTHER INFORMATION: Sequence of the E2 transmembranal domain
     of the Sindbis viral glycoprotein after deleting amino acids 376
     through 380, the resulting deletion mutant is TM21.

<400> SEQUENCE: 26

His Pro Val Tyr Thr Ile Leu Ala Val Ala Ser Ala Thr Gly Val

-continued

```
                 5                  10                  15
Thr Val Ala Val Leu Cys Ala Cys
                20

<210> SEQ ID NO 27
<211> LENGTH: 22
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino acids 376 through
      381, the resulting deletion mutant is TM20.

<400> SEQUENCE: 27

His Pro Val Tyr Thr Ile Leu Ala Val Ala Ser Ala Thr Val Thr
                 5                  10                  15
Val Ala Val Leu Cys Ala Cys
                20

<210> SEQ ID NO 28
<211> LENGTH: 21
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino acids 372 through
      378, the resulting deletion mutant is TM19.

<400> SEQUENCE: 28

His Pro Val Tyr Thr Ile Leu Ala Val Met Ile Gly Val Thr Val
                 5                  10                  15
Ala Val Leu Cys Ala Cys
                20

<210> SEQ ID NO 29
<211> LENGTH: 20
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino acids 372 through
      379, the resulting deletion mutant is TM18.

<400> SEQUENCE: 29

His Pro Val Tyr Thr Ile Leu Ala Val Ile Gly Val Thr Val Ala
                 5                  10                  15
Val Leu Cys Ala Cys
                20

<210> SEQ ID NO 30
<211> LENGTH: 19
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino acids 372 through
      380, the resulting deletion mutant is TM17.

<400> SEQUENCE: 30

His Pro Val Tyr Thr Ile Leu Ala Val Gly Val Thr Val Ala Val
                 5                  10                  15
Leu Cys Ala Cys

<210> SEQ ID NO 31
<211> LENGTH: 18
```

-continued

```
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino acids 372 through
      381, the resulting deletion mutant is TM16.

<400> SEQUENCE: 31

His Pro Val Tyr Thr Ile Leu Ala Val Val Thr Val Ala Val Leu
                5                   10                  15

Cys Ala Cys

<210> SEQ ID NO 32
<211> LENGTH: 16
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino acids 373 through
      384, the resulting deletion mutant is TM14.

<400> SEQUENCE: 32

His Pro Val Tyr Thr Ile Leu Ala Val Ala Ala Val Leu Cys Ala
                5                   10                  15

Cys

<210> SEQ ID NO 33
<211> LENGTH: 14
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino acids 371 through
      384, the resulting deletion mutant is TM12.

<400> SEQUENCE: 33

His Pro Val Tyr Thr Ile Leu Ala Ala Val Leu Cys Ala Cys
                5                   10

<210> SEQ ID NO 34
<211> LENGTH: 12
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino acids 369 through
      384, the resulting deletion mutant is TM10.

<400> SEQUENCE: 34

His Pro Val Tyr Thr Ile Ala Val Leu Cys Ala Cys
                5                   10
```

What is claimed is:

1. A genetically engineered virus selected from the group consisting of Alphavirus, Flavivirus and Bunyavirus which is capable of infecting and producing progeny virus in insect cells, and is capable of infecting but not producing progeny virus in mammalian cells, said engineered virus comprises an envelope transmembrane protein selected from the group consisting of glycoprotein E1, glycoprotein E2, glycoprotein E and glycoprotein G that is able to span or correctly integrate into the cell membrane of insect cells but not that of mammalian cells due to deletion of one or more amino acids in the transmembrane region of said envelope transmembrane protein.

2. The genetically engineered virus of claim 1, wherein said insect cells are mosquito cells.

3. The genetically engineered virus of claim 2, wherein said mosquito cells are *Aedes albopictus* cells.

4. The genetically engineered virus of claim 1, wherein said mammalian cells are human cells.

5. The genetically engineered virus of claim 1, wherein said virus is Sindbis virus, and said transmembrane protein is viral glycoprotein E2.

6. The genetically engineered virus of claim 5, wherein said virus is selected from the group consisting of ΔK391 virus and TM16 virus, said ΔK391 virus has a lysine deletion at position 391 of the virus glycoprotein E2, and said TM16 virus has 10 amino acids deleted in the virus glycoprotein E2.

* * * * *

UNITED STATES PATENT AND TRADEMARK OFFICE
CERTIFICATE OF CORRECTION

PATENT NO. : 6,589,533 B1
DATED : July 8, 2003
INVENTOR(S) : Dennis T. Brown and Racquel Hernandez It is certified that error appears in the above-identified patent and that said Letters Patent is hereby corrected as shown below:

Column 1,
Line 10, please delete the period after the word "of".

Column 2,
Line 6, please delete the space in "a s".

Column 4,
Line 12, please delete the hyphen after "particles".
Line 57, please delete the period after "chromosomes".
Line 57, please remove the capitalization of "In".

Column 6,
Line 58, "readilypredict" should be two words.

Column 7,
Line 31, please delete the comma after "produce".
Line 49, "subcutaneusly" should read -- subcutaneously --.

Column 10,
Line 1, "$\mu$ were" should read -- $\mu$1 were --.
Line 41, please insert a period after the word "min".

Column 12,
Line 28, please insert a period after "ER".

Column 14,
Line 11, "cell" should read -- cells --.
Line 23, "fourth" should read -- forth --.
Line 56, "or" should read -- for --.

Column 15,
Line 26, "utants" should read -- mutants --.
Line 59, please insert a space before the word "Cholesterol".

UNITED STATES PATENT AND TRADEMARK OFFICE
CERTIFICATE OF CORRECTION

PATENT NO. : 6,589,533 B1
DATED : July 8, 2003
INVENTOR(S) : Dennis T. Brown and Racquel Hernandez It is certified that error appears in the above-identified patent and that said Letters Patent is hereby corrected as shown below:

<u>Column 16,</u>
Line 16, please insert a space after the word "Brown".

Signed and Sealed this

Thirtieth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,589,533 B1
DATED : July 8, 2003
INVENTOR(S) : Dennis T. Brown and Racquel Hernandez It is certified that error appears in the above-identified patent and that said Letters Patent is hereby corrected as shown below:

<u>Column 1,</u>
Between lines 14 and 15, insert
-- The United States government may own certain rights to this invention pursuant to grant number AI 42775 from National Institutes of Health. --.

Signed and Sealed this

Tenth Day of January, 2006

JON W. DUDAS
*Director of the United States Patent and Trademark Office*